United States Patent [19]

Rosevear et al.

[11] 4,385,991
[45] May 31, 1983

[54] AFFINITY CHROMATOGRAPHY SEPARATION PROCESS

[75] Inventors: Alan Rosevear, Faringdon; Patrick Mattock, Botley, both of England

[73] Assignee: United Kingdom Atomic Energy Authority, England

[21] Appl. No.: 192,831

[22] Filed: Oct. 1, 1980

Related U.S. Application Data

[63] Continuation of Ser. No. 28,595, Apr. 9, 1979, abandoned, which is a continuation of Ser. No. 858,749, Dec. 8, 1977, abandoned.

[30] Foreign Application Priority Data

Dec. 15, 1976 [GB] United Kingdom ............... 52434/76

[51] Int. Cl.³ ............................................. B01N 15/08
[52] U.S. Cl. ..................................... 210/635; 210/656
[58] Field of Search ..................... 210/635, 656, 198.2; 252/426, 428

[56] References Cited

U.S. PATENT DOCUMENTS

| | | | |
|---|---|---|---|
| 3,943,072 | 3/1976 | Thompson | 252/455 R |
| 3,947,352 | 3/1976 | Cuatrecasas | 210/635 |
| 3,983,299 | 9/1976 | Regnier | 210/198.2 |
| 4,029,583 | 6/1977 | Chang | 210/198.2 |
| 4,045,353 | 8/1977 | Kosaka | 210/198.2 |
| 4,143,201 | 3/1979 | Miyashiro et al. | 210/198.2 |
| 4,162,355 | 7/1979 | Tsibais | 210/635 |

Primary Examiner—John Adee
Attorney, Agent, or Firm—Larson and Taylor

[57] ABSTRACT

The invention discloses a process for the selective separation of a chemical component from a fluid substance which comprises contacting the fluid substance with a composite material having affinity chromatography properties, said composite material comprising an affinity chromatography agent retained within the pore structure of a porous rigid support material and said affinity chromatography agent being capable of selectively sorbing the chemical component from the fluid substance.

13 Claims, 1 Drawing Figure

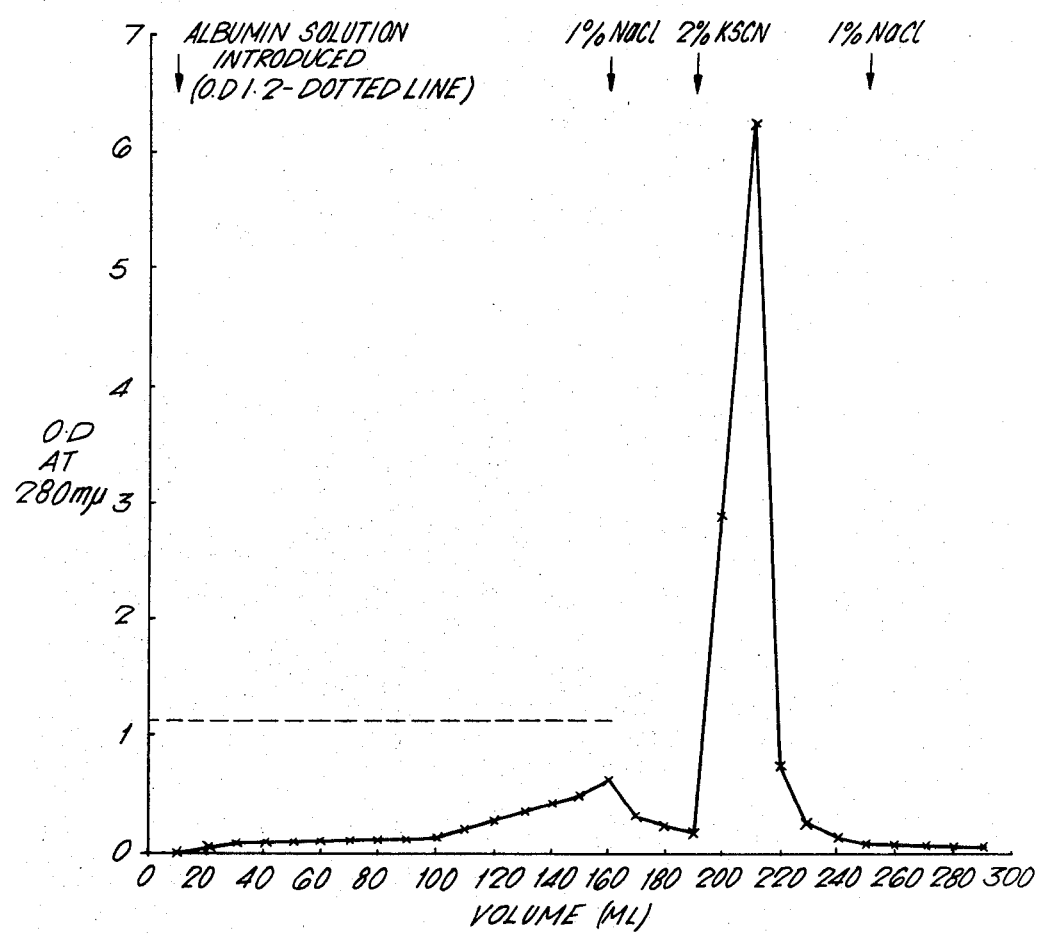

AFFINITY CHROMATOGRAPHY SEPARATION PROCESS

This is a continuation of the application Ser. No. 28,595, filed Apr. 9, 1979, which is a continuation of Ser. No. 858,749, filed Dec. 8, 1977, both now abandoned.

The present invention relates to separating processes and more particularly to processes for separating chemical components from a mixture of components in fluid substances.

According to the present invention there is provided a process for the selective separation of a chemical component from a fluid substance which comprises contacting the fluid substance with a composite material having affinity chromatography properties, said composite material comprising an affinity chromatography agent retained within the pore structure of a porous rigid support material and said affinity chromatography agent being capable of selectively sorbing the chemical component from the fluid substance.

By "affinity chromatography agent" we mean a substantially insoluble material having ligands capable of selectively sorbing a given chemical component from a mixture of components in a fluid substance (e.g. in solution), the sorbing being a result of interactions between a specific site or sites on the given chemical component with a particular site or sites on the ligand. Accordingly when a material is said to have "affinity chromatography properties" it means that it is capable of selectively sorbing a given chemical component from a mixture of components in a fluid substance by means of interaction between a particular site or sites on ligands on the material and a specific site or sites on the given chemical component.

Affinity chromatography agents have been used particularly in the separation and purification of water soluble components where the nature of the interaction between agent and components is of a biochemical nature or involves biochemical molecules. Techniques of affinity chromatography are described in "Methods in Enzymology" volume 34, Edited by W. B. Jakoby and M. Wicheck Academic Press (1975).

It will be understood that the sorbed component may be subsequently recovered from the composite material for example by contacting the composite material with a solution of a reagent capable of desorbing the component therefrom.

Preferably the affinity chromatography agent is, or is part of, a deformable gel and the composite material accordingly comprises the deformable gel retained within the pore structure of the porous rigid support material.

We prefer that the composite material having affinity chromatography properties is a composite material in accordance with British patent application No. 52433/76 (the subject matter of which is incorporated in a U.S. Continuation-in-part application (of even date herewith) of U.S. patent application Ser. No. 730,706 now abandoned which discloses inter alia:

"A composite material comprising a deformable gel retained within the pore structure of a porous rigid support material wherein an affinity chromatography agent is, or is part of, the deformable gel such that the composite material is a composite material having affinity chromatography properties."

A detailed discussion of the composite materials and methods for the preparation thereof will be found in the continuation-in-part hereinbefore mentioned, the disclosure of which is hereby incorporated by reference into this specification.

By "deformable gel" we mean a gel which itself is a non-rigid material (e.g. a xerogel). Such deformable gels include organic polymeric materials and certain inorganic materials, for example, silicic acid.

Preferably the porous rigid support material is in the form of discrete porous particles having an interconnected pore structure (for example those particles of inorganic material which may be prepared in accordance with British patent application No. 58374/74 (now British Pat. No. 1,421,531 (corresponding to U.S. patent is U.S. Pat. No. 3,943,072)) e.g. discrete porous particles of a natural earth, such as Celite or Keiselguhr.

The term "aerogel" has been used in the art to describe a rigid, preformed matrix containing pores and this term and the term "xerogel" are discussed in "An Introduction to Permeation Chromatography" by R. Epton and C. Holloway issued by Koch-Light Laboratories Limited.

The continution-in-part application hereinbefore mentioned also discloses methods for making composite materials having affinity chromatography properties. Reference may be made to the disclosure of the continuation-in-part for details but for convenience we set out brief details below:

Thus, inter alia the continuation-in-part application discloses a method for preparing a composite material of a deformable gel having affinity chromatography properties retained within the pore structure of a porous rigid support material comprising introducing a precursor for the gel into the pore structure of a porous rigid support material and treating the precursor to form and retain the deformable gel in the pore structure.

Also the continuation-in-part application discloses a method for preparing a composite material of a deformable gel having affinity chromatography properties retained within the pore structure of a porous rigid support material, which method includes the step of treating an inactive deformable gel retained within the pores of a porous rigid support material to impart affinity chromatography properties to the inactive deformable gel.

By "inactive deformable gel" in the present Specification we mean a deformable gel having little or no useful affinity chromatography properties.

The inactive deformable gel can be treated to have affinity chromatography properties by modifying the inactive gel or by adding further species (e.g. ligands) thereto.

In view of the foregoing statements in this specification it will be appreciated that the invention disclosed in the above mentioned continuation-in-part application is concerned, inter alia with the provision of a rigid "skeleton" having dimensional stability as a support for a non-rigid deformable gel.

Thus, for use in accordance with the present invention, deformable gels which have, or can be treated to have, useful affinity chromatography properties, but which are difficult or inconvenient to handle because of their non-rigid nature (and therefore tending to undergo dimensional changes when subjected to pressures normally found in column operation (e.g. up to ~3 atmospheres) and deform to cause an increase in back pressure) are incorporated into a composite material in accordance with the continuation-in-part application, which material, due to the rigidity imparted by the porous rigid support "skeleton", can be handled and used more easily.

Thus where the composite material comprises, for example discrete porous particles with a deformable gel retained therein the composite materials can be loaded into and used, conveniently in column systems.

It is to be understood that the majority of the deformable gel formed in accordance with the continuation-in-part application hereinbefore mentioned will be present in the internal pore structure of the porous rigid support material, but also it should be noted that some gel may be formed on the surface of the support material.

An important feature of the invention of the continuation-in-part application is that there is produced a composite material in which there is the minimum of deformable gel outside of the internal pore structure of the porous rigid support material. Thus, where the porous rigid support material is in the form of discrete porous particles there is a minimum of deformable gel formed between the particles, and substantially all of the deformable gel formed is retained by the particles with the majority of the deformable gel being in the internal pore structure thereof, so that the resulting composite material is in the form of discrete particles such as to aid, inter alia, handling, column packing and column operation.

Loosely adhering deformable gel may be removed from the particles of composite material by washing and, if necessary mechanical means (e.g. sieving).

To assist in maximising the amount of the deformable gel, or inactive deformable gel, retained in the pore structure of the porous rigid support material where, in accordance with an embodiment of the method of the invention of the continuation-in-part application hereinbefore mentioned a solution of precursor in contacted with the porous rigid support material to introduce precursor into the pore structure, we prefer that the volume of the solution of precursor contacted with the support material (e.g. by soaking the support material in the solution) is approximately equal to the volume required to fill the pore structure. It will be appreciated that to minimise the amount of deformable gel, or inactive deformable gel, formed outside the pore structure the volume of the solution should not exceed the volume required to fill the pore structure. Also we prefer that the volume of any reagent solutions used to treat the precursor in the pore structure to form a gel is not substantially in excess of that required to immerse the porous rigid support material.

The chemical component to be selectively separated may be, for example, a protein such as albumin.

The inactive deformable gel may be a nentrol polyol (e.g. PV Alcohol or agarose) or a gel which can be treated to be non-sorptive per se. Where the affinity chromatography agent is part of a deformable gel, it will be appreciated that other constituents of the deformable gel in the finished composite should not have sorptive properties, since such properties could compete with the affinity chromatography agent.

As hereinbefore disclosed the deformable gel may be an organic polymeric material. Examples of organic polymeric materials which can be formed as inactive gels in the pore structure of a porous rigid support material and subsequently treated to add further species thereby to impart affinity chromatography properties are polysaccharide gels (e.g. agarose gels and cellulose gels), and synthetic polymer gels such as polymers of acrylates, and polyvinyl alcohol polymer gels.

An example of a composite material in accordance with the continuation-in-part application hereinbefore mentioned and suitable for use in accordance with the present invention is discrete porous particles of celite (prepared in accordance with British Pat. No. 1,421,531 (U.S. Pat. No. 3,943,072)) having retained within the pore structure thereof an agarose gel to which has been coupled the dye "Cibacron Blue 3G-A" (ex Ciba-Geigy). Cibacron dye is an affinity chromatography ligand capable of retaining proteins (e.g. albumin) from human plasma and the structure of this dye is given hereinafter.

Examples of other composite materials in accordance with the above mentioned co-pending application which are suitable for use in accordance with the present invention are discrete porous particles of celite (prepared in accordance with British Pat. No. 1,421,531 (U.S. Pat. No. 3,943,072)) having retained within the pore structure thereof a polymer gel to which has been coupled the dye Cibacron Blue 3G-A, the polymer gel being a methacrylate, an acrylamide or a polyvinyl alcohol gel.

The present invention also provides a chemical component when separated from a fluid substance by a process in accordance with the present invention.

It has been found that good flow properties are obtainable in columns with substantially spherical particles of composites.

It will be appreciated that the deformable gel and porous rigid support material should be substantially insoluble in fluid substances with which they may be contacted in use (e.g. solutions containing chemical components to be sorbed and eluting agent solutions).

Cibacron Blue 3G-A is a group specific ligand and is known to interact specifically with the nucleotide binding site of certain enzymes (e.g. kinases and dehydrogenases).

It will be appreciated that other affinity chromatography ligands may be coupled to the deformable gel within the porous rigid support material. Examples of such ligands are described in "Methods in Enzymology" Volume 34 hereinbefore mentioned.

The structure of Cibacron Blue 3G-A is as follows:

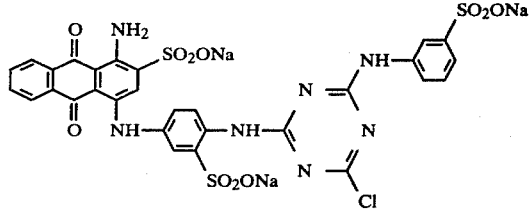

U.S. Pat. No. 3,943,072 discloses and claims, inter alia,

"A method for producing an inorganic material having interconnected porosity throughout the material for the selective retention of predetermined molecules from a fluid substance containing said molecules including the steps of: mixing a finely divided, substantially insoluble, sorptive, inorganic material, capable of sorbing the molecules, with a solid fugitive additive to form a mixture, including in the mixture a solvent to dissolve fugitive additive in the solvent, said inorganic material being substantially insoluble in said solvent, forming discrete particles from the mixture, and heating the particles to remove solvent and fugitive additive to produce discrete particles of said inorganic material having an interconnected pore structure throughout said discrete particles providing an extended surface area, the pore size being such as will allow said predetermined molecules in said fluid substance to permeate the inorganic particles and be sorbed, said inorganic material being substantially unaffected by said heating utilized to effect removal of solvent and fugitive additive."
and also claims an inorganic material made by the method claimed in U.S. Pat. No. 3,943,072.

Discrete porous particles (for example those fabricated from a finely divided substantially insoluble, sorptive inorganic material in accordance with U.S. Pat. No. 3,943,072) for use in accordance with the invention disclosed in the continuation-in-part application hereinbefore mentioned preferably have a porosity of $>20\%$ and an interconnected porosity with pores $\geq 2000$ A such as to allow both deformable gel and macromolecules (e.g. proteins or enzymes) to occupy the pores.

"Celite" (Registered Trade Mark) as hereinbefore mentioned is a natural diatomaceous earth produced by Johns-Manville Corporation.

The invention will now be further described by way of example only with reference to Examples 1 to 5, and 11 to 20 which show the preparation of composites suitable for use in accordance with the invention, Examples 6 to 10 and 21 which show the separation of proteins in accordance with the invention, Examples 22 to 24, and the single FIGURE of the accompanying drawing which is a chromatogram showing separation of albumin as described in Example 10.

EXAMPLE 1

A hot aqueous solution of agarose (4% w/v) was mixed with porous celite particles (prepared in accordance with British Pat. No. 1,421,531 (U.S. Pat. No. 3,943,072); 400–700 $\mu$dia) until the porous particles were completely filled. The mixture was boiled for 5 minutes and excess liquid poured off the particles. The agarose was gelled by pouring the particles into a fluidised bed of cold water.

The agarose in the porous particles was cross-linked as follows:

The particles were washed on 0.5 M caustic soda solution and then reacted with epichlorhydrin (10 ml) in 0.5 M caustic soda (50 ml) for $2\frac{1}{2}$ hrs. at 60°. The resulting slurry was agitated at intervals to distribute the epichlorhydrin.

The resulting particles of agarose/celite composite (which were shown by pyrolysis of a sample thereof to have an 8.8% organic content) were treated to introduce affinity chromatography properties thereto by the covalent coupling an affinity chromatography dye to the agarose.

Thus, 5 mls of the composite were washed in water, the water was decanted and 5mls of water added. The composite was heated to 60° C. and a solution of Cibacron Blue 3G-A in water (4% w/v, 1 ml) was added and the particles and solution mixed. After 15 minutes sodium chloride (0.5g) was added, the mixture was heated to 90° C. and a solution of sodium carbonate (10% w/v, 1 ml) added.

After 1 hour at 90° C. the blue particles were washed and stored.

EXAMPLE 2

10 ml of a solution containing hydroxethyl methacrylate (1.1 ml) and bis acrylamide (0.015 g) in 0.1 M tris buffer (pH 7.5) were dry mixed with porous celite particles (15 ml) (of the kind used in Example 1). The mixture was deaerated and purged with nitrogen before being irradiated with 1 Megarad of $\gamma$-radiation. The particles were washed and found to contain 12.4% organic material. The composite particles were treated as with Cibacron Blue 3G-A as in Example 1.

EXAMPLE 3

A mixture of 50 ml of hot 10% aqueous polyvinyl alcohol and porous celite particles (of the kind used in Example 1) (75 ml) were added to cold acetone to precipitate polyvinyl alcohol in the particles. The particles were then reacted with epichlorhydrin (5ml) and 0.5M caustic soda in 1:1 aqueous acetone (25 ml) at room temperature for $4\frac{1}{2}$ hrs. (The organic content as determined by pyrolysis of a sample thereof was 9.8%).

The composite was treated with Cibacron Blue 3G-A as in Example 1 to give deep blue composite particles.

EXAMPLE 4

A hot aqueous agarose solution (4% w/v (50 ml) and porous celite particles (prepared in accordance with our British Pat. No. 1,421,531 (U.S. Pat. No. 3,945,072; 200–400$\mu$ dia) (75 ml were mixed together and allowed to cool thereby to form an agarose gel within the celite particles. Any agglomerations were broken down by lightly brushing through a 1200 mesh sieve.

The agarose was then cross-linked by the following procedure.

The agarose/celite composite was added to an emulsion (prewarmed to 60° C.) formed by stirring together 50 ml 1 MNaOH, 10 mls epichlorhydrin and 2.5 g "TWEEN 20" (surfactant).

The composite and emulsion were kept at 60° C. for 2 hours and the composite subsequently was found (by pyrolysis of a sample thereof) to contain 10.1% organic material.

The composite was washed and the supernatent solution decanted from the particles. A solution of Cibacron Blue 3G-A dye (ex Ciba Geigy UK) (40 mg/ml, 20 ml) was mixed with the particles and the resulting slurry heated to 60° C.

Sodium chloride (5 g) was mixed with the slurry. After 15 minutes a 10% solution of sodium carbonate (10 ml) was added and the slurry heated to 90° C. for 1 hour.

The resulting blue composite of celite/agarose/Cibacron dye was washed and stored as an aqueous slurry.

EXAMPLE 5

A solution of cellulose acetate to acetone (5 ml), 8% was soaked into 10 ml porous celite particles (of the kind used in Example 1) and the cellulose acetate precipitated by adding water (15 ml.) The cellulose acetate (ester) was saponified with 10 ml 1 M caustic soda for 6 hours. The organic content of the composite was 6.3%.

A sample of the resulting composite was treated with Cibacron Blue 3G-A as in Example 1 to give blue composite particles.

EXAMPLE 6

A sample of particles prepared as in Example 1 was investigated with respect to its capacity to remove albumin from solution.

Thus, the particles were mixed with a solution of dilute human albumin (1 mg protein/ml) in 3% sodium chloride solution. After 20 minutes the particles were washed, the protein desorbed with an equal volume of 400 mM potassium thiocyanate in 1% sodium chloride solutions and the soluble protein estimate by its adsorption at 280 nm. The $E_{10}^{280}$ value was 0.388 ($E_{10}^{280}$ is Optical Density at 280 m in a 10 mm cell).

EXAMPLE 7

A sample of particles prepared as in Example 2 were tested as in Example 6 with regard to albumin removal properties. The $E_{10}^{280}$ of the thiocyanate extract was ~0.181.

EXAMPLE 8

A sample of particles prepared as in Example 3 were tested as in Example 6 with regard to albumin removal properties.

The $E_{10}^{280}$ of the thiocyanate extract was 0.100.

EXAMPLE 9

A sample of composite particles prepared as in Example 5 were tested as in Example 6 with regard to albumin removal properties.

The $E_{10}^{280}$ of the thiocyanate was 0.308.

EXAMPLE 10

A sample of celite/Agarose/Cibacron dye composite particles prepared as in Example 4 were packed into a column (1.5 cm dia × 10 cm length).

The column was washed with 1% aqueous NaCl solution, then with a solution of 2% KSCN in 1% aqueous sodium chloride and finally with 1% aqueous NaCl again to remove any weakly bound dye and equilibrate the column.

A solution optical density of 1.2 (280 nm) containing 1 mg/ml human albumin (purity 90%) in 0.05 M tris citrate buffer (pH 7.0) was pumped through the column for 2 hours at 50 ml/hr and the eluate from the column monitored for protein content by means of OD measurements at 280 m.

During the 2 hour period the eluate showed a low level of non-albumin material absorbing at 280 m.

Introduction of further albumin containing solution to the column lead to a rapid rise in the OD of eluate from the column which indicated that saturation of the composite with absorbed albumin had been achieved.

The column was washed for 1 hour with 50 ml of 1% aqueous sodium chloride solution to remove unabsorbed materials and subsequently the absorbed albumin was eluted using 2% KSCN (in 1% aqueous NaCl solution).

The amount of albumin eluted corresponded to a capacity of about 10 mg albumin/ml of composite particles.

The eluted albumin was found to be substantially free from the impurities present in the starting solution, the impurities being passed through the column without being retained.

A chromatogram showing OD of eluate from the column against volume of solution passed through the column is shown in the single FIGURE of the accompanying drawing.

The points of introduction of albumin solution, NaCl solutions and thiocyanate eluting solution are marked on the chromatogram.

The region where unabsorbed albumin began to appear in the eluate from the column (indicating partial saturation of the composite) can be seen in the chromatogram beginning after 100 ml of eluate had passed through the column and peaking at 160 mls.

The column had good flow properties as illustrated by the ability to pass 50 ml/hr of solution.

EXAMPLE 11

A hot aqueous solution (~90° C.) of agarose (4% w/v) was mixed with 50 ml porous celite particles (prepared in accordance with British Pat. No. 1,421,531 (U.S. Pat. No. 3,945,072) (250–425 μdia) until the porous particles were just filled (33 ml). The resulting mixture was maintained at 90° C. for 15 minutes before cooling to room temperature.

The agarose in the porous particles was cross-linked as follows:

A mixture was prepared by adding 10 ml epichlorhydrin to 50 ml of 1 M NaOH containing 5% v/v TWEEN 20 and emulsifying. 60 ml of this mixture were preheated to 60° C. and added to the agarose containing particles (preheated to 60° C.). After standing for 2½ hrs. at 60° C. with occasional stirring, the particles were washed until neutral pH was obtained.

The resulting particles of agarose/celite composite (shown by pyrolysis of a sample thereof to have a 3% by weight organic content) were treated to introduce affinity chromatography properties thereto by the covalent coupling of an affinity chromatography agent (Cibacron Blue 3GA dye) to the agarose.

Thus, after washing, as much water as possible was removed from the particles by decantation of the supernate and then they were heated to 90° C. 20 ml of 4% Cibacron Blue 3GA dye (preheated to 90° C.) was added to the particles followed by 5 g of solid sodium chloride. After 15 minutes 10 ml of a 10% (w/v) sodium carbonate (preheated to 90° C.) was added and mixed and the resulting mixture left for 1 hour at 90° C. with occasional stirring.

The resultant dyed composite was allowed to cool, any aggregates were broken down by gentle sieving, and the particles washed to remove traces of excess dye.

EXAMPLE 12

The procedure of Example 11 was followed with the exceptions that the cross-linking procedure was omitted and the treatment with Cibacron Blue 3GA dye was conducted at 70° C. for 3 hours instead of 90° C. for 1 hour.

EXAMPLES 13–16

The procedure of Example 11 was followed with the exceptions that the concentration of the agarose starting solution was respectively 1% (Example 13), 2% (Example 14), 3% (Example 15) and 5% (Example 16).

EXAMPLES 17–20

The procedure of Example 12 was followed with the exception that the concentration of the agarose starting solution was respectively 1% (Example 17), 2% (Example 18), 3% (Example 19) and 5% (Example 20).

EXAMPLE 21

The albumin adsorption capacity of a sample of each of the composite materials produced as in Examples 13 to 20 were investigated and the results are presented in the following Table.

| Example No. | % agarose | Albumin capacity* |
|---|---|---|
| 13 | 1 | 8.5 |
| 14 | 2 | 12.5 |
| 15 | 3 | 14.5 |
| 16 | 5 | 12.4 |
| 17 | 1 | 5.0 |
| 18 | 2 | 8.0 |
| 19 | 3 | 10.5 |
| 20 | 5 | 10.5 |

[*Albumin capacity is given in mg albumin/ml packed bed]

It will be appreciated that an increase in the concentration of agarose in the starting solution leads to an increase in agarose in the composite.

The albumin capacity was investigated in a manner similar to that set out in Example 10.

The albumin capacity figures obtained indicate (i) (when plotted as a curve) that there is an optimum agarose conveniently for albumin capacity at ~3% wt agarose in the composite (corresponding to a 4% w/v agarose starting solution) for both cross-linked and uncross-linked composite materials and (ii) the albumin capacity of composite material produced with cross-linking is higher than that of composite material produced without cross-linking.

EXAMPLE 22

A sample of composite material prepared as in Example 11 was used to treat a sample of Fraction IV (a fraction derived from Cohn ethanol precipitation of plasma) containing albumin (38% by wt), transferrin (25% by wt) at IgG (8% by wt).

The treatment was carried out in a column in a manner similar to that of Example 10.

Following the sorption of albumin onto the composite material the column was eluted with KSCN solution to recover an eluate containing predominantly albumin. The eluate showed a 7.5-fold reduction in transferrin content and an 8.9-fold reduction in IgG over the starting sample.

EXAMPLE 23

Water was passed through a column of composite material particles (as produced in Example 11) at several pressures to investigate the flow properties.

The column size was 1.45×9.2 cm. The flow rates at various pressures were as follows:

| Pressure (inches H$_2$O) | Flow rate (ml/hr) |
|---|---|
| 20 | 300 |
| 40 | 500 |
| 60 | 700 |
| 80 | 900 |

We claim:

1. A chromatography process for the selective separation of a chemical component from a fluid substance which comprises contacting the fluid substance with a composite material having affinity chromatography properties, said composite material comprising an inorganic porous rigid support material having within the pores thereof a deformable gel to which is coupled an affinity chromatography ligand being capable of selectively sorbing the chemical component from the fluid substance, the outside surface of said support being substantially free of said deformable gel.

2. A process as claimed in claim 1 wherein the porous rigid support is in the form of discrete porous particles.

3. A process as claimed in claim 2 wherein the discrete porous particles are those prepared by a method for producing an inorganic material having interconnected porosity throughout the material for the selective retention of predetermined molecules from a fluid substance containing said molecules including the steps of mixing a finely divided, substantially insoluble, sorptive, inorganic material, capable of sorbing the molecules, with a solid fugitive additive to form a mixture, including in the mixture a solvent to dissolve fugitive additive in the solvent, said solvent, forming discrete particles from the mixture, and heating the particles to remove solvent and fugitive additive to produce discrete particles of said inorganic material having an interconnected pore structure throughout said discrete particles providing an extended surface area, the pore size being such as will allow said predetermined molecules in said fluid substance to permeate the inorganic particles and be sorbed, said inorganic material being substantially unaffected by said heating utilized to effect removal of solvent and fugitive additive.

4. A process as claimed in claim 2 wherein the discrete porous particles are discrete particles of a natural earth.

5. A process as claimed in claim 1 wherein a component of the deformable gel is an affinity chromatography agent comprising a group specific ligand capable of interacting specifically with the nucleotide binding sites of an enzyme.

6. A process as claimed in claim 1 wherein a component of the deformable gel is an affinity chromatography agent comprising an affinity chromatography ligand capable of retaining proteins from human plasma.

7. A process as claimed in claim 1 wherein a component of the deformable gel is a polysaccharide gel or a synthetic polymer gel.

8. A process as claimed in claim 7 wherein the polysaccharide gel is an agarose or a cellulose gel.

9. A process as claimed in claim 7 wherein the synthetic polymer gel is a polymer of an acrylate or a polyvinyl alcohol gel.

10. A process as claimed in claim 1 wherein the composite material is in the form of substantially spherical particles.

11. A process as claimed in claim 1 wherein the chemical component is albumin.

12. A process as claimed in claim 1 wherein the chemical component is subsequently recovered from the composite material by contacting the composite material with a solution of a reagent capable of desorbing the chemical component therefrom.

13. A chemical component whenever separated from a fluid substance by a process as claimed in claim 1.

* * * * *